US00PP08911P

United States Patent [19]

Davidson

[11] Patent Number: Plant 8,911

[45] Date of Patent: Sep. 27, 1994

[54] HYBRID TEA ROSE PLANT NAME HADFLARE

[76] Inventor: Harvey D. Davidson, #3 El Verano Rd., Orinda, Calif. 94563

[21] Appl. No.: 143,580

[22] Filed: Oct. 15, 1993

[51] Int. Cl.[5] ..... A01H 5/00

[52] U.S. Cl. ..... Plt./20

[58] Field of Search ..... Plt. 20, 11, 16, 17

*Primary Examiner*—Howard J. Locker

[57] ABSTRACT

A new rose variety of the Hybrid Tea class characterized by having large well formed orange-red flowers on a bush with very glossy foliage and excellent disease resistance.

1 Drawing Sheet

The present invention relates to a new and distinctive variety of rose plant of the Hybrid Tea class, which was originated by my crossing 'Shining Ruby' as the seed parent with (Smooth Sailing×Futura—U.S. Plant Pat. No. 3,569,) as the pollen parent.

Among the novel characteristics possessed by the new variety which distinguish it from its:

(a) Parents and all other varieties of which I am aware are:
  (1) A very floriferous plant with glossy foliage.
  (2) A large orange-red flower.
  (3) Very disease resistant and vigorous.

(b) Seed parent: Red flowers.

(c) Pollen parent; Light-orange flowers; matte foliage.

Asexual reproduction of the new rose variety by budding, as performed at Tulare, Calif. shows that the aforementioned and all other distinctive characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in the color description herein refers to plate numbers in the aforementioned color chart, e.g., "53A" is plate "53A" of the Royal Horticultural Society Colour Chart.

Parentage:

*Seed parent.*—'Shining Ruby'.

*Pollen parent.*—(Smooth Sailing×Futura—U.S. Plant Pat. No. 3,569).

Class: Hybrid Tea.

The following observations are made of specimens grown outdoors in Contra Costa County, Calif., in the month of September.

FLOWER

Blooming habit:

A. Bud:
  (1) *Size.*—Fully mature, sepals enclosed, 20–23 mm from base of sepals.
  (2) *Form.*—Ovoid.
  (3) *Sepals.*—22 to 24 mm in length; 8–10 mm extension beyond bud; no serration shown on sepal edges. Generally 2 out of 5 sepals show appendages on each side, 2 to 4 mm length; heavy cotton mating on inner surface of sepals. Smooth on outer surface. Glandular development on sepal edges. Outside color — 181A, areas of 146B; inside — 146C.
  (4) *Peduncle.*—Length — 6 to 7 cm; Surface — smooth, no prickles, a few glandular hairs. Strength — stiff, slight curvature. Color — 181A, occasional areas of 146C.
  (5) *Receptacle.*—Shape — rounded, 10–12 mm. Color — 146C.
  (6) *Color.*—Sepals folded outside petals — near 66D, shadings of 47D; immediate opening, inside petals near shadings of 43B and 43C.

B. Bloom:
  (1) *Size.*—Average when open — 8 to 10 cm.
  (2) *Borne.*—1 to 3.
  (3) *Form.*—Globular; opens in loose manner.
  (4) *Petalage.*—Average number — 22 to 24.
  (5) *Color.*—Early open near 43B and C inside; near 47C and D outside. Fully open near 43C and D, and 42C inside; near 47C and D outside.

C. Petals;
  (1) *Texture.*—Firm.
  (2) *Appearance.*—Flexed; satiny.
  (3) *Form.*—Rounded; base to top edge; 4.5 cm; horizontal center: 5.5 cm.
  (4) *Arrangement.*—Loose, somewhat irregular.
  (5) *Petaloids in center.*—Average 1 to 2.
  (6) *Persistence.*—Drop off cleanly.
  (7) *Fragrance.*—Strong.
  (8) *Lasting quality.*—On plant 6–7 days; cut 4–5 days.

REPRODUCTIVE ORGANS

A. Stamen:
  (1) *Arrangement.*—Regularly arranged around styles.
  (2) *Number.*—Average 175 to 185.
  (3) *Length.*—Average — 8 to 10 mm.
  (4) *Filaments.*—Color — Close to 45D.
  (5) *Anthers.*—Color — 25C.
  (6) *Pollen.*—25C.

B. Pistil:
  (1) *Styles.*—5 to 6 cm length; number 90 to 95; few fine white hairs; color: near 155A. with shadings of 43C.
  (2) *Stigma.* —Color — close to 155A.

(3) *Ovary.*—6–7 mm through center.

C. Hips:

*Mature.*—(1) Size: 20–25 mm; color: near 21A. (2) Achenes: average 4–6 per hip.

PLANT

A. Form: upright.

B. Growth: Vigorous; medium height: average 80–100 cm.

C. Stem length: Basal break to flower bud tip: average — 60 cm.

D. Foliage: Compound of 3 to 5 leaflets on bloom stem; 5 to 7 leaflets on main canes.

(1) *Mature size, 5 leaflet.*—Tip of terminal leaflet to stipule base 15–16 mm.

(2) *Quantity.*—Stems well covered.

(3) *Color.*—New foliage upper side 146B; under side 146C. Old foliage upper side 146A; under side 146B.

(4) *Shape.*—Oval with center pointed.

(5) *Texture.*—Firm, very leathery, glossy.

(6) *Edge.*—Fine serration on outer edge. Average 5 points per 1 cm, with up to 1 mm peak.

(7) *Rachis.*—Glandular hair on upper side; lower side: 3 to 4 hooked prickles 2 mm length, spaced near to 2 cm apart.

(8) *Stipules.*—Length 2 cm; auricle to 5 mm. Edge of stipule to tip of auricle with many glandular hairs.

E. Resistance to disease; Mildew, rust, blackspot: excellent.

F. Wood:

*New wood.*—Color 146C. Bark — smooth.

*Old wood.*—Color 146A. Bark — smooth.

G. Thorns:

(1) *Shape.*—Sharp pointed with slight downward curvature.

(2) *Color.*—Near to 177C.

(3) *Spacing.*—Average 24–30 per 30 cm.

H. Winter hardiness: very good.

I claim.

1. A new and distinct variety of rose plant of the hybrid tea class, substantially as herein shown and described.

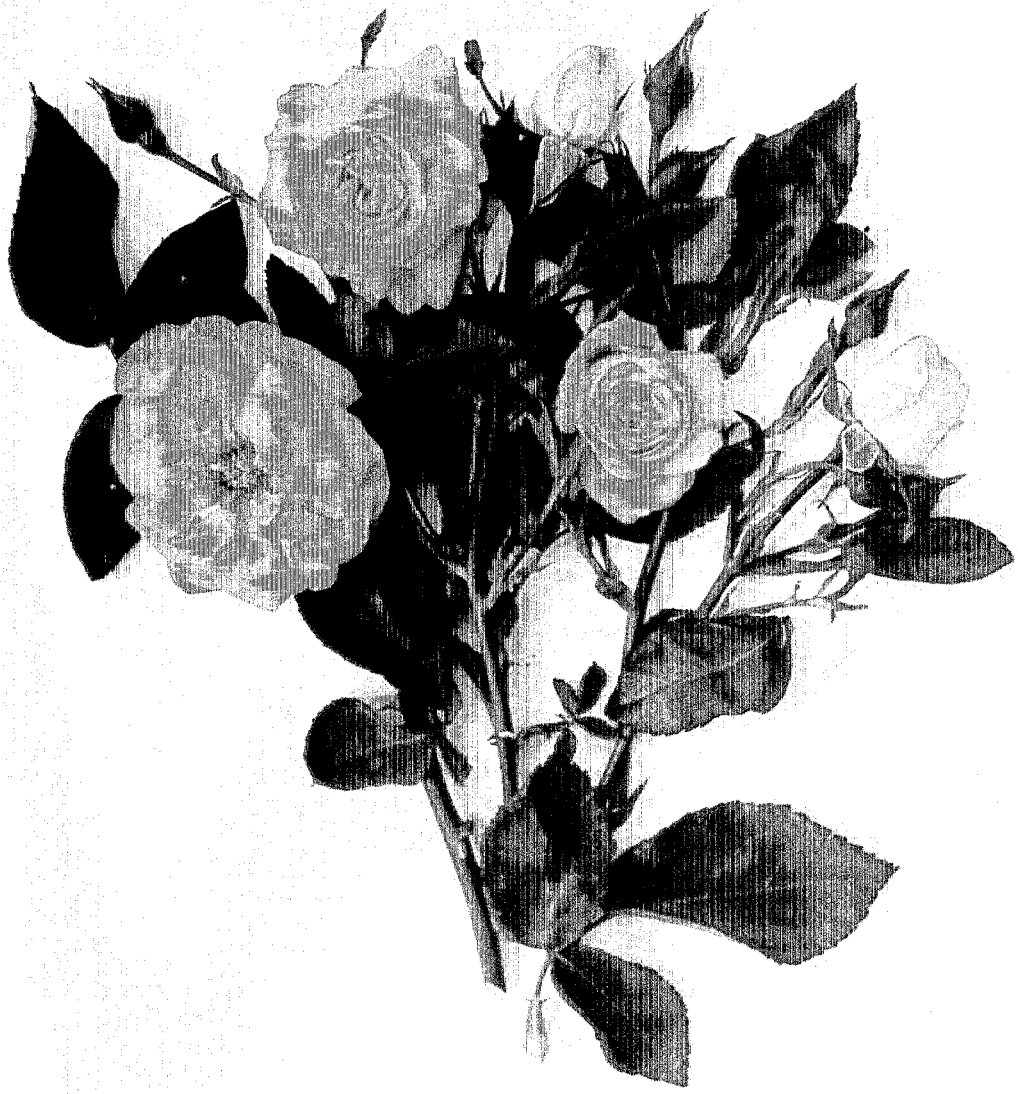

* * * * *